US00PP26067P3

(12) United States Plant Patent
Van Rosmalen

(10) Patent No.: US PP26,067 P3
(45) Date of Patent: Nov. 10, 2015

(54) ***PHALAENOPSIS* ORCHID PLANT NAMED 'PHALFIMWAQ'**

(50) Latin Name: ***Phalaenopsis* Blume**
Varietal Denomination: PHALFIMWAQ

(71) Applicant: ANTHURA B.V., Bleiswijk (NL)

(72) Inventor: Nicolaas Arnoldus Maria Van Rosmalen, Velp (NL)

(73) Assignee: ANTHURA B.V., Bleiswijk (NL)

( * ) Notice: Subject to any disclaimer, the term of this patent is extended or adjusted under 35 U.S.C. 154(b) by 156 days.

(21) Appl. No.: 13/998,205

(22) Filed: Oct. 10, 2013

(65) Prior Publication Data

US 2015/0106989 P1 Apr. 16, 2015

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

(56) References Cited

PUBLICATIONS

Enclosure for the Plant Patent application of Anthura BV, 13 pages.

*Primary Examiner* — Anne Grunberg
(74) *Attorney, Agent, or Firm* — Jondle & Associates, P.C.

(57) ABSTRACT

A new and distinct variety of *Phalaenopsis* plant named 'PHALFIMWAQ', particularly characterized by yellow flowers with yellow-orange-white lip, 2 to 3 peduncles, a long and sturdy inflorescence, a narrow obovate leaf shape, and propagated by tissue culture is disclosed.

3 Drawing Sheets

Genus and species: *Phalaenopsis* Blume.
Variety denomination: 'PHALFIMWAQ'.

BACKGROUND OF THE NEW PLANT

The present invention comprises a new and distinct cultivar of *Phalaenopsis* plant, botanically known as *Phalaenopsis* of the Orchidaceae family, and hereinafter referred to by the cultivar name 'PHALFIMWAQ'.

*Phalaenopsis* comprises a genus of about 60 species of herbaceous perennials many of which, or the hybrids thereof, are suitable for cultivar in the home or greenhouse. *Phalaenopsis* is predominantly epiphytic or rock dwelling, and is native to tropical Asia, the Malay Archipelago, and Oceania. The species typically has 2-ranked, fleshy, oblong or elliptic leaves affixed to a short central stem (monopodial growth), which vary in size from 12 to 20 cm to over 60 cm. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petals, called the labellum, is three-lobed and is often more brightly-colored than the other flower segments. Flower colors include various shades of pink, white, yellow, and red-brown.

*Phalaenopsis* orchids are typically propagated from seeds. Asexual propagation of *Phalaenopsis* is often done from off-shoots which arise from the lower bracts of the inflorescence. The resulting plants are detached from the mother plants and may be planted in a suitable substrate.

The new *Phalaenopsis* 'PHALFIMWAQ' is particularly characterized by its attractive and unique yellow flowers, economical propagation by tissue culture, rapid growth, and a plant dimension suitable for packaging and shipping to the market.

'PHALFIMWAQ' is a product of a planned breeding program conducted in Bleiswijk, The Netherlands.

The new *Phalaenopsis* 'PHALFIMWAQ' originated from a cross made in August 2006 in Bleiswijk, The Netherlands. The female parent is a yellow *Phalaenopsis* pot plant named '21368-02' (unpatented), while the male parent is a white *Phalaenopsis* pot plant named '01-1630' (unpatented). A single plant was selected in August 2009 and has been asexually reproduced repeatedly by tissue culture in Bleiswijk, The Netherlands over a 3-year period. The new variety has been found to retain its distinctive characteristics through successive asexual propagations.

Asexual reproduction of 'PHALFIMWAQ' by tissue culture was first performed in May 2012 in Bleiswijk, The Netherlands and has demonstrated that the new cultivar is firmly fixed and retained through successive generations of asexual reproduction.

Plant Breeder's Rights for this variety have been applied for in Europe on Jan. 15, 2013. 'PHALFIMWAQ' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands.

1) Yellow flower with yellow-orange-white lip;
2) 2 to 3 peduncles;
3) Inflorescence is long and sturdy;
4) The shape of the leaf is narrow obovate; and
5) Plants are propagated by tissue culture.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs are of a 50-week old plant grown in a greenhouse in Bleiswijk, The Netherlands in March 2013.

DESCRIPTION OF THE NEW VARIETY

Figure 1:
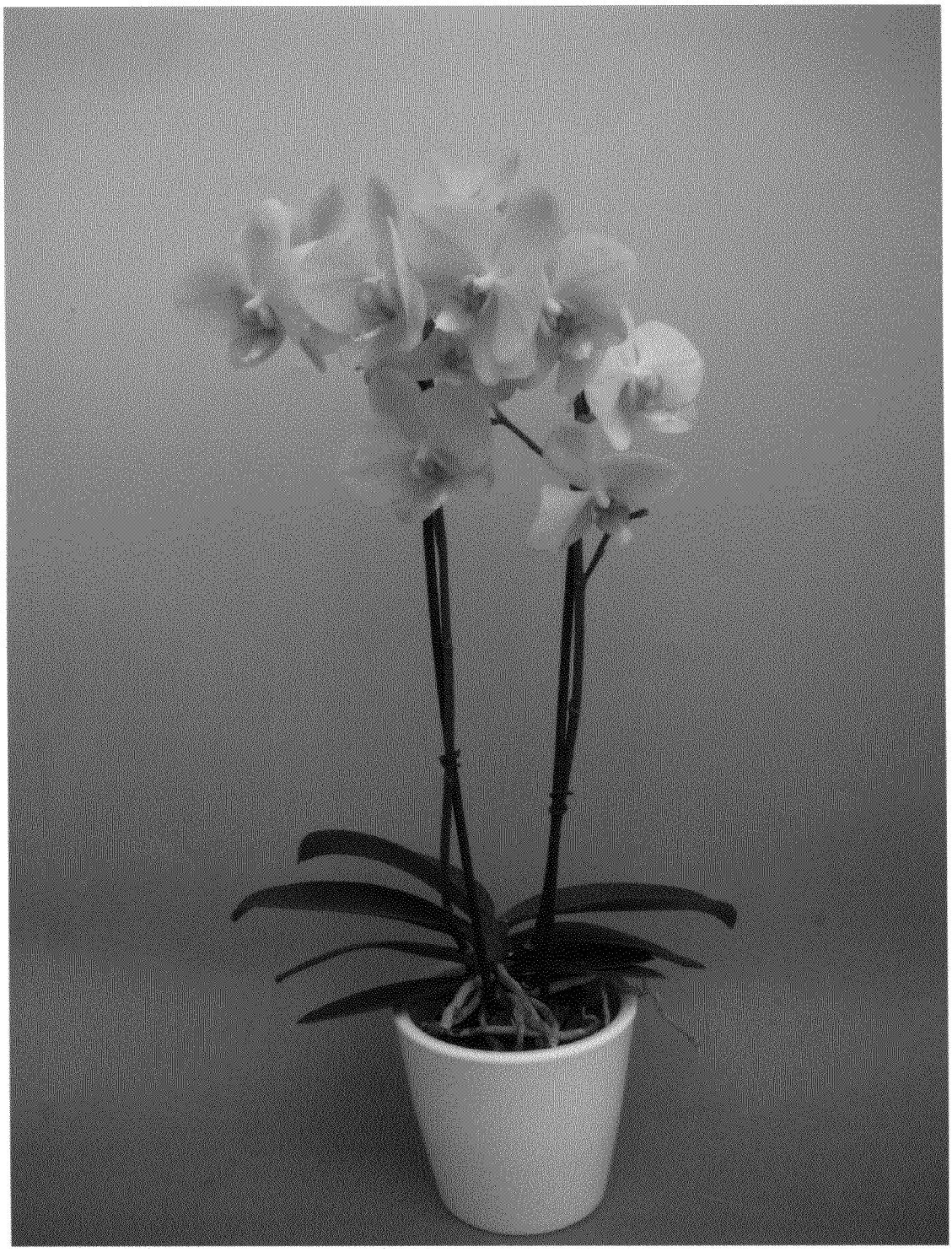
FIG. 1 shows the overall plant habit, including blooms and foliage of 'PHALFIMWAQ'.
Figure 2:
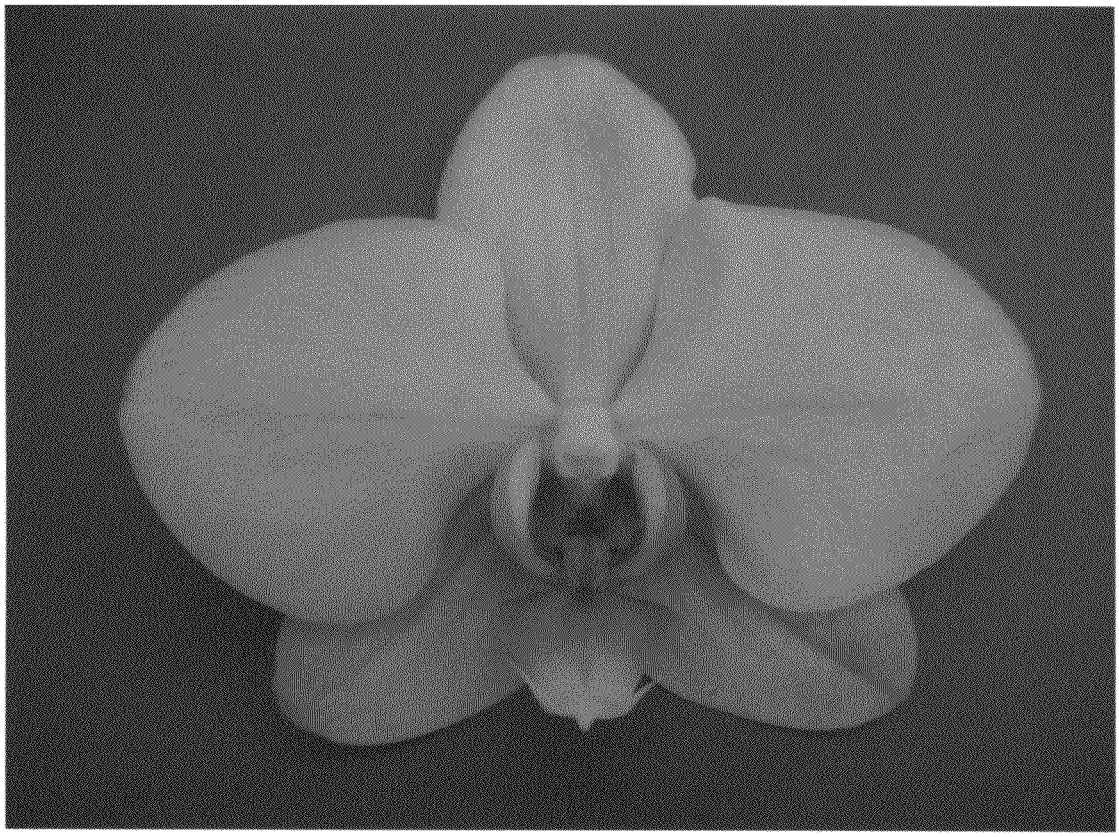
FIG. 2 shows a close-up of the flower of 'PHALFIMWAQ'.
Figure 3:
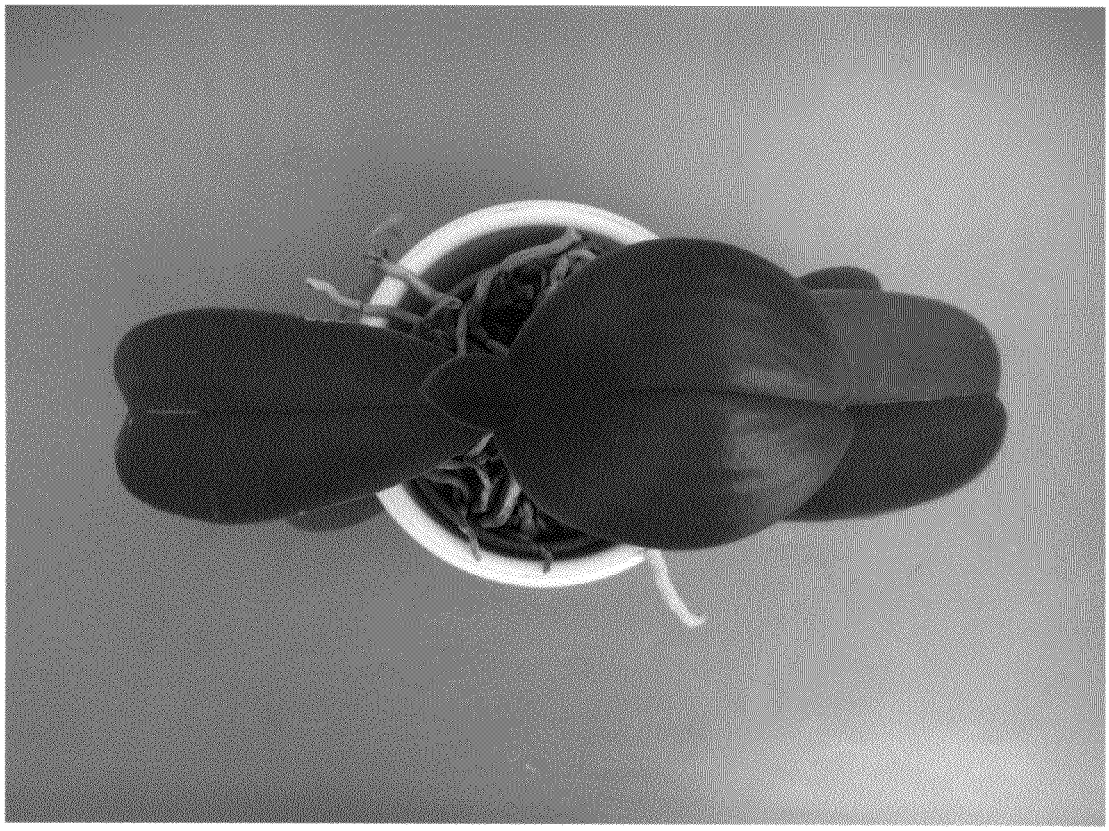
FIG. 3 shows a close-up of the leaves of 'PHALFIMWAQ'.

The following detailed description sets forth the distinctive characteristics of 'PHALFIMWAQ'. The data which define these characteristics were collected from asexual reproductions carried out in Bleiswijk, The Netherlands. The plant history was taken on 50-week old plants which were planted from tissue culture in 12 centimeter pots and grown in a greenhouse between 27° C. to 29° C. for 30 weeks, continued by a cooling period of 8 weeks between 18° C. to 20° C. and 12 weeks in a greenhouse of 21° C. Observations were made in March 2013. Color readings were taken under 4000 to 6000 lux natural light in the greenhouse. Color references are primarily to The R.H.S. Colour Chart of The Royal Horticultural Society of London (R.H.S.) (2001).

DETAILED BOTANICAL DESCRIPTION

Classification:
- *Family.*—Orchidaceae.
- *Botanical.*—*Phalaenopsis* Blume.
- *Common name.*—*Phalaenopsis.*
- *Variety name.*—'PHALFIMWAQ'.

Parentage:
- *Female parent.*—*Phalaenopsis* cultivar '21368-02' (unpatented).
- *Male parent.*—*Phalaenopsis* cultivar '01-1630' (unpatented).

Propagation:
- *Type.*—Tissue culture.

Plant:
- *Crop time* (*time to produce a finished flowering plant*).—48 to 50 weeks for a 12 cm pot.
- *Growth habit of inflorescence.*—Standard type, dark green leaves and normal raceme.
- *Height* (*including pot, including inflorescence*).—60.0 cm to 65.0 cm.
- *Width* (*measured from leaf tips*).—32.0 cm to 35.0 cm.
- *Vigor.*—Moderate to strong.

Roots:
- *Root description.*—Grey-green-colored roots with branching lateral roots having grey-green-colored root tips.

Leaves:
- *Mature leaves.*—Quantity per plant: 8 to 9 leaves are produced before flowering. Length (fully expanded): 16.0 cm to 19.0 cm. Width: 7.0 cm to 8.0 cm. Shape: Narrow obovate. Apex: Obtuse. Leaf blade angle with the petiole: Between 10 degrees and 20 degrees. Leaf margin: Entire. Color: Upper surface: RHS 137A. Lower surface: RHS 138B. Texture: Smooth and slightly rough. Thickness: 2.0 mm. Venation: Pattern: Parallel. Color of the midvein: Upper surface: RHS 136B. Lower surface: RHS 141D.

Peduncle:
- *Quantity per plant.*—2 to 3.
- *Number of flowers per peduncle.*—10 to 18.
- *Length.*—50.0 cm.
- *Diameter.*—About 0.5 cm.
- *Strength.*—Moderate to strong.
- *Aspect.*—Upright.
- *Texture.*—Smooth.
- *Color.*—Brown/dark green (RHS 147A).
- *Internode length.*—50.0 mm to 100.0 mm.

Inflorescence description:
- *Appearance.*—Upright to slightly pendant, raceme inflorescence with bilaterally symmetrical flowers that open in succession beginning with the lowermost flower.
- *Inflorescence size.*—Height (from base to tip): 140.0 mm to 160.0 mm. Diameter: 170.0 mm to 190.0 mm.
- *Flowering time.*—First flowers can be expected 10 to 11 months after planting in a 12 cm pot.
- *Flower.*—Height: 80.0 mm to 90.0 mm. Diameter: 90.0 mm to 100.0 mm. Depth of lip: 25.0 mm to 27.0 mm.
- *Flower longevity.*—On the plant: 8 to 12 weeks.
- *Fragrance.*—Absent.
- *Petals.*—Arrangement: Open. Shape: Semi-circular. Apex: Mucronate and symmetric. Margin: Entire. Length: 44.0 mm to 46.0 mm. Width: 45.0 mm to 47.0 mm. Color (when fully opened): Main color: Yellow (RHS 4D). At the base: Yellow (RHS 4D).
- *Dorsal sepal.*—Shape: Elliptic. Length: 45.0 mm to 47.0 mm. Width: 30.0 mm to 32.0 mm. Color (when fully opened): Main color: Yellow (RHS 4D). At the base: Yellow (RHS 4D).
- *Lateral sepals.*—Shape: Ovate. Length: 28.0 mm to 30.0 mm. Width: 44.0 mm to 47.0 mm. Color (when fully opened): Main color: Yellow (RHS 4D). At the base: Yellow with a touch of green (RHS 4D; 1B).
- *Labellum* (*lip*).—Margin: Entire. Length: 22.0 mm to 24.0 mm. Width: 17.0 mm to 19.0 mm.
- *Lateral lobe.*—Shape: type V. Color: White with yellow shade and red stripes (RHS 155D; 17B; 34B).
- *Apical lobe.*—Shape: Obdeltoid. Color: White with yellow shade and orange shade (RHS 155D; 14B; 171A).
- *Callus.*—Color: Orange (RHS 23A).

Reproductive organs:
- *Arrangement.*—The stamens, style and stigmas are fused into a single, short structure called the column, possessing one terminal anther with pollen grains united into pollinia, which are covered by an anther cap. The stigma is located under the column behind the pollinia. The ovary is inferior with three carpels present.
- *Column.*—Length: 11.0 mm to 12.0 mm. Diameter: 5.0 mm to 6.0 mm. Color: White (RHS 155D).
- *Pollinia.*—Quantity: 2. Size: 1.2 mm to 1.3 mm. Color: Orange (RHS 26A).
- *Ovary.*—Length: 9.0 mm to 10.0 mm (cut open). Diameter: 4.5 mm to 5.5 mm.

*Pedicel.*—Length: 34.0 mm to 38.0 mm. Diameter: 3.0 mm to 4.0 mm.

Disease, pest, and stress resistance: No specific resistance or susceptibility observed.

Temperature tolerance: Tolerant to a low temperature of 15° C. and a high temperature about 30° C.

COMPARISON WITH PARENTAL AND COMMERCIAL VARIETIES

'PHALFIMWAQ' differs from female parent '21368-02' (unpatented) in that 'PHALFIMWAQ' has a callus that is moderately raised, a flower that has a lighter yellow-green color, a white column, and a weakly spatulate (type IV) lateral lobe, whereas '21368-02' has a callus that is almost flat or slightly raised, a darker yellow flower color, a light purple and white column, and an oblong (type III) lateral lobe. Additionally, 'PHALFIMWAQ' has a larger flower than '21368-02'.

'PHALFIMWAQ' differs from male parent '01-1630' (unpatented) in that 'PHALFIMWAQ' has a yellow flower, a weakly spatulate (type IV) lateral lobe, and a weak curvature of the lateral lobe, whereas '01-1630' has a white flower, a spatulate (type V) lateral lobe, and a strong curvature of the lateral lobe. Additionally, the flower of 'PHALFIMWAQ' has a center, whereas the flower of '01-1630' is even.

'PHALFIMWAQ' differs from commercial variety 'PHALCUZOL' (unpatented) in that 'PHALFIMWAQ' has an apical lobe of the lip that is yellow with a greyed-orange edge towards the callus and white color towards the whiskers, whereas 'PHALCUZOL' has an apical lobe of the lip that is red-purple with light purple and white towards the whiskers. In addition, 'PHALFIMWAQ' has a flower with a light green-yellow color that has a small, slightly light purple center, whereas 'PHALCUZOL' has a flower with a slightly darker yellow color that has a larger, white center. Further, 'PHALFIMWAQ' has longer whiskers of the lip than 'PHALCUZOL'.

I claim:

1. A new and distinct variety of *Phalaenopsis* plant named 'PHALFIMWAQ' as illustrated and described herein.

* * * * *